United States Patent [19]

Kaartinen et al.

[11] 4,116,632

[45] Sep. 26, 1978

[54] COUNTERCURRENT COMBUSTION SYSTEM FOR PREPARING RADIOACTIVE SAMPLES AND THE LIKE

[75] Inventors: Niilo H. Kaartinen; Pentti J. Juhala, both of Kuusisto, Finland

[73] Assignee: Packard Instrument Company, Inc., Downers Grove, Ill.

[21] Appl. No.: 801,861

[22] Filed: May 31, 1977

[51] Int. Cl.[2] ....................... G01N 31/12; G01N 33/16

[52] U.S. Cl. .............................. 23/230 PC; 23/230.3; 422/78

[58] Field of Search ......... 23/230 PC, 253 PC, 230.3, 23/230.6; 431/3

[56] References Cited

U.S. PATENT DOCUMENTS

| | | | |
|---|---|---|---|
| 2,809,100 | 10/1957 | Krasl | 23/230 PC X |
| 2,888,332 | 5/1959 | Aites | 23/253 PC |
| 3,002,819 | 10/1961 | Brace et al. | 23/253 PC |
| 3,844,716 | 10/1974 | Noakes | 23/230 PC |
| 3,868,221 | 2/1975 | Howard et al. | 23/253 PC X |
| 3,923,464 | 12/1975 | Sitek et al. | 23/230 PC |
| 3,942,938 | 3/1976 | Kaartinen | 23/230 PC X |

*Primary Examiner*—Joseph Scovronek
*Attorney, Agent, or Firm*—Leydig, Voit, Osann, Mayer & Holt, Ltd.

[57] ABSTRACT

A system for combusting materials containing radioactive nuclides to permit recovery of the radioactive nuclides includes a combustion zone for combusting a sample material containing at least one radioactive nuclide. The combustion products are continuously exhausted from one end of the combustion zone, and a continuous pressurized stream of oxygen-containing gas is introduced into the combustion zone between the exhaust end of the zone and the sample during the combustion thereof. At least a portion of the pressurized oxygen-containing gas stream is directed through the combustion zone in a spiral path toward the sample to circulate at least a portion of the combustion products around the combustion zone as they flow toward the exhaust end of the zone counter to the flow of the spiraling stream of oxygen-containing gas, thereby intimately mixing the combustion products with the oxygen-containing gas in the combustion zone.

18 Claims, 4 Drawing Figures

COUNTERCURRENT COMBUSTION SYSTEM FOR PREPARING RADIOACTIVE SAMPLES AND THE LIKE

DESCRIPTION OF THE INVENTION

The present invention relates to analytical combustion systems for combusting materials containing radioactive nuclides to permit recovery of the radioactive nuclides and, more particularly, to analytical combustion systems of the type used in laboratory equipment for separating radioactive nuclides from samples of tissue and the like.

In recent years, flame combustion systems have become increasingly popular for the preparation of analytical samples for radioactive nuclide studies. Analytical combustion systems of this general type have been disclosed in my U.S. Pat. Nos. 3,485,565; 3,542,121; 3,682,598; 3,761,228; 3,830,628; 3,849,069; and 3,979,503. Although these systems have been sold commercially for several years now, they still require time-consuming treatment or preparation of the sample materials before they are combusted and/or the use of relatively small samples of certain materials in order to achieve adequate combustion. For example, fatty tissue samples and the like must be limited in size and mixed with a carrier material such as cellulose powder to achieve complete combustion. Without samples combustion, recovery of the radioactive nuclides is incomplete, resulting in undesirable "memory" (retention of radioactive material) in the apparatus and consequent spillover errors which adversely affect the anlaytical results.

In my recent U.S. Pat. No. 3,942,938, an improved two-zone combustion system is described for achieving rapid and complete combustion of even the most difficult samples by use of a particular type of secondary combustion zone.

It is a principal object of the present invention to provide an improved primary analytical combustion system which can be used alone or in combination with a secondary combustion zone. The improved primary combustion system is safe to operate even in a fully automatic system which is left unattended, and it also achieves complete sample combustion. As in the case of the secondary combustion device described in my U.S. Pat. No. 3,942,938, my new primary combustion system achieves the improved results without utilizing a catalytic packing or filling, thereby avoiding the high back pressure, slow heat transfer, and poisoning problems that often result from the use of such catalytic materials.

Another important specific object of this invention is to provide such an improved analytical combustion system which is capable of completely combusting difficult samples (e.g., fatty samples, diluted samples, samples with large surface areas, volatile samples, diluted gas etc.) efficiently without any prior treatment or preparation of the sample material, and which is capable of rapidly combusting liquid or wet samples. In this connection, a particularly important object of the invention is to provide a combustion system which is capable of completely combusting a wide variety of different samples under standardized conditions, thereby permitting automatic operation for a wide variety of different applications.

One of the important specific objects of the invention is to provide such an improved analytical combustion system which is capable of safely combusting very volatile samples so that the system can be safely left unattended during automatic operation.

It is another object of the invention to provide such an improved combustion system which, in combination with commercially available recovery systems, is capable of achieving radioactive nuclide recoveries of 99% and higher with negligible memories attributable to pyrolysis products.

Another object of the invention is to provide such an improved analytical combustion system which achieves high heat transfer rates and such complete combustion that the exhaust products are essentially free of smoke, soot or other particulate combustible matter.

A further important object of the invention is to provide such an improved analytical combustion system without any contribution to the combustion products by the container for the sample being combusted, so that the entire capacity of the recovery system can be used to recover compounds of interest from the sample itself. In this connection, a related object of the invention is to provide such a system which is capable of handling samples as large as 5 to 6 grams, using presently existing commercial recovery systems.

Yet another significant object of the invention is to provide such an improved analytical combustion system which facilitates the removal from the combustion zone of any ash or residue remaining at the end of each combustion cycle.

A still further object of the invention is to provide such a system which does not require any special ignition system for initiating combustion of the sample.

Still another object of the invention is to provide such an improved combustion which utilizes compact and simple equipment so that it can be efficiently manufactured at a reasonable cost, and so that it can be contained in a relatively compact housing.

A further object of the invention is to provide an improved analytical combustion system of the type described above which has a long operating life, and which is more efficient, more reliable, less expensive, and faster than analytical combustion systems proposed heretofore.

Yet another important object of the invention is to provide such an improved combustion system which can be fabricated without any joints in the combustion zones.

Other objects and advantages of the invention will be apparent from the following detailed description together with the accompanying drawings, in which.

Figure 1:
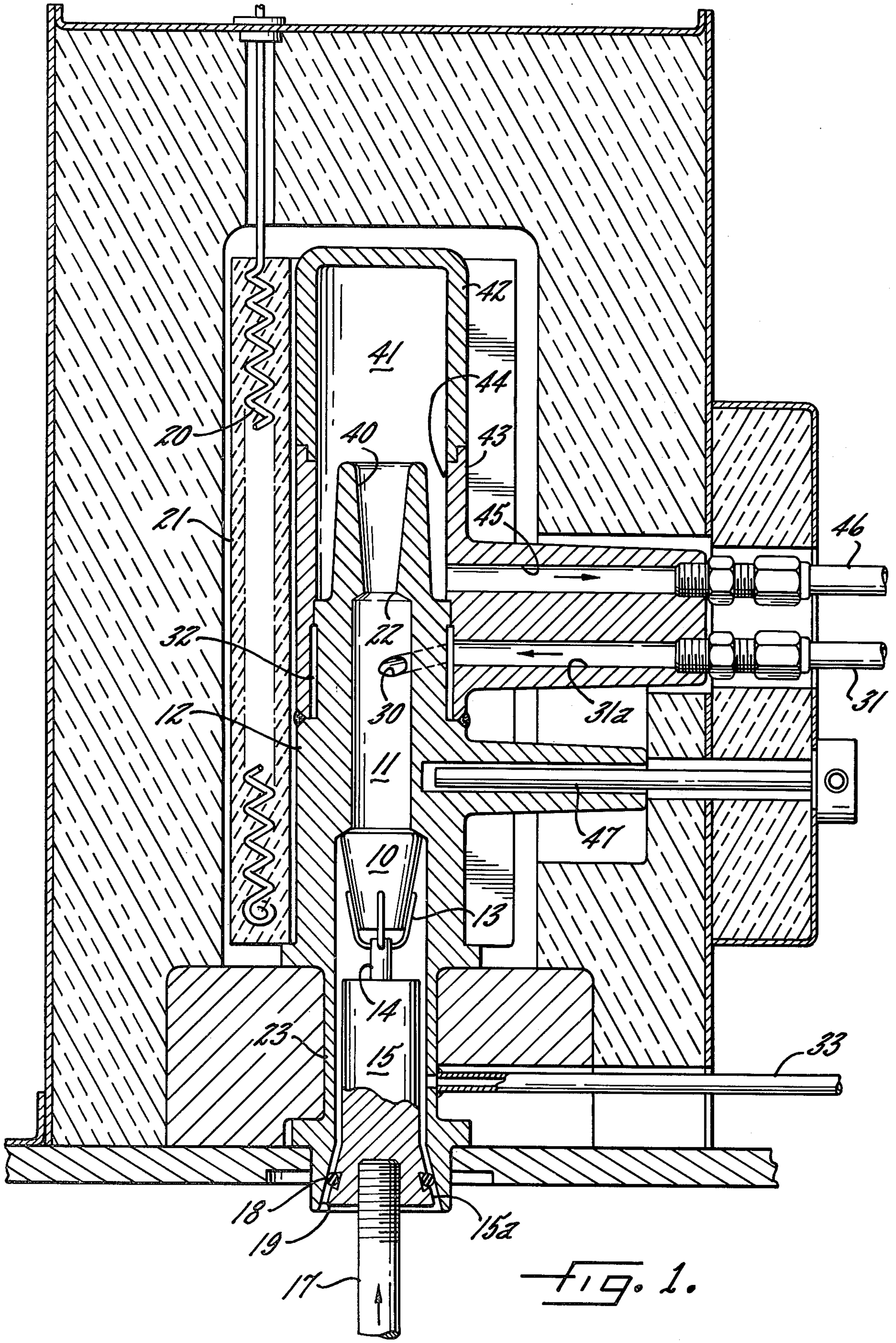
FIG. 1 is a sectional side elevation of an analytical combustion system embodying the invention.

While the invention will be described in connection with a certain preferred embodiment, it will be understood that is is not intended to limit the invention to that embodiment. On the contrary, it is intended to cover all alternatives, modifications, and equivalents as may be included within the spirit and scope of the invention as defined by the appended claims.

Turning now to the drawings, there is illustrated an analytical combustion system for use in the preparation of samples for radioactive nuclide tracer studies, such as studies involving tissue distribution and residue levels of drugs in plants and animals. In the preparation of such samples, the sample material containing the radioactive nuclide tracer, such as plant or animal tissue, is combusted to convert the carbon in the starting materials to carbon dioxide and the hydrogen to water, and the radioactive nuclide tracer is then recovered as a combustion product. The details of suitable radioactive nuclide recovery systems are described in my aforementioned patents and applications and will not be repeated here. Suffice it to say that the combustion unit is followed by various units, interconnecting conduits, and associated apparatus for treating the gaseous combustion products to separate and effect recovery of selected radioactive nuclides. The apparatus in this instance is particularly adapted for recovery of 3H and 14C tracers. As used herein and in the appended claims, the term "combustion" refers not only to flame combustion but also to oxidation, pyrolysis, vaporization or any other process that converts the sample material into gaseous or vaporous products from which the radioactive nuclides can be separately recovered; and the term "combustion products" refers to the gaseous or vaporous products released from the sample material by any of these combustion mechanisms.

At the beginning of a combustion cycle, material containing the radioactive nuclide or nuclides, in either solid or liquid form, is placed in a ceramic crucible 10, and a preprogrammed pneumatic control unit (not shown) positions the crucible 10 at the lower end of a primary combustion zone 11 formed by a metal cylinder 12. The crucible 10 is supported by a plurality of fingers 13 secured to a rod 14 projecting upwardly from a cylindrical metal platform 15. To facilitate the loading of successive samples for combustion, the platform 15 is threaded or otherwise secured to the end of a pneumatic piston rod 17. This rod 17 forms a part of a retracting and elevating mechanism (not shown) which automatically moves the sample crucible 10 from a retracted position easily accessible to the operator (not shown in the drawings) to an advanced position within the combustion zone 11 as shown in the drawings. In this advanced position, an O-ring 18 carried by a flared base portion **15*a* of the platform is pressed against a complementary tapered wall 19 at the bottom of the cylinder 12** so as to seal the bottom of the combustion chamber.

For the purpose of heating the sample in the crucible 10 to the temperature required to combust the sample, which temperature is preferably in the range of from about 700° C. to about 1000° C., a high temperature electric heater 20 within a ceramic shell 21 is disposed around the upper portion of the cylinder 12 that forms the primary combustion zone 11. This heater 20 is electrically insulated from the metal cylinder 12 by the ceramic shell 21 to prevent the electric heating current from being conducted into the metal cylinder. When the heater 20 is energized, it heats the outside wall of the cylinder 12 which conducts the heat to the walls of the combustion zone 11. The sample within the crucible 10 is heated by both radiant heat and convection. As the sample is combusted, the combustion products rise upwardly through the combustion zone 11 and exit through an exhaust port 22 which has a diameter considerably smaller than that of the combustion zone 11.

At the lower end of the cylinder 12, the walls of the cylinder are made much thinner than the walls of the upper portions of the cylinder, as at 23 in FIG. 1, so as to minimize the conduction of heat to the lower end of the cylinder. That is, the thin wall 23 at the lower end of the cylinder 12 functions as a "heat dam" which serves to retain as much heat as possible in the upper regions of the cylinder where it is needed for combustion of the sample, and the regions below the heat dam remain relatively cool to prolong the life of the O-ring 18. It will be appreciated that these variable wall thicknesses in the unitary metal cylinder can be easily formed by conventional machining operations.

Figure 4:
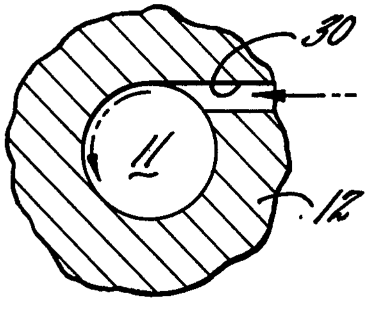
FIG. 4 is a section taken along line 4—4 in FIG. 2.

In accordance with one important aspect of the present invention, a pressurized stream of oxygen-containing gas is introduced into the primary combustion zone between the sample and the exhaust end of the combustion zone, and at least a portion of the oxygen-containing gas stream is directed through the combustion zone in a spiral path toward the sample to circulate at least a portion of the combustion products around the combustion zone as they flow toward the exhaust end of the zone counter to the flow of the spiraling stream of oxygen-containing gas. Thus, in the illustrative system, a pressurized stream of substantially pure oxygen is fed into the combustion zone 11 through a tangential feed port 30 located near the top of the combustion zone. To produce the desired downward spiraling flow of the incoming oxygen, the port 30 is directed downwardly at a slight angle and on a tangent to the walls of the combustion chamber 11 (see FIG. 4). It is not critical that the oxygen feed port 30 be directed downwardly, because the restricted exhaust port 22 causes at least a portion of the oxygen to flow downwardly through the combustion zone 11 even when the feed port 30 is oriented horizontally or at a slight upward angle. Oxygen is supplied to the port 30 from a pressurized source connected to a supply line 31 leading to a conduit **31*a* and manifold chamber 32 extending around the entire circumference of the cylinder 12 adjacent the outer end of the port 30**.

The oxygen flow rate is initially adjusted, by suitable valving and flow metering means (not shown), to a level slightly above that required to support stoichiometric combustion of the sample, so that there is a slight excess of oxygen near the feed port 30 within the combustion zone 11. A typical initial feed rate is 4 liters/minute. The oxygen is introduced into the combustion zone 11 at a relatively high initial velocity, e.g., about 18,000 cm/sec. (35000 ft/min.) for a 1-mm. orifice, or 8000 cm/sec. for a 1.5-mm. orifice, which decreases as the oxygen spirals downwardly through the upwardly flowing combustion products. The downwardly flowing oxygen is gradually consumed in the combustion process, with any oxygen remaining at the bottom of the zone becoming entrained in the upward flow of the combustion products.

The increasing consumption of the oxygen as it flows downwardly through the combustion zone 11 produces an oxygen gradient within the combustion. That is, the oxygen level is at a maximum near the feed port 30, where the degree of mixing and turbulence is also at a maximum, and the oxygen level diminishes in the lower regions of the combustion zone, where the degree of mixing and turbulence also diminishes. Thus, an optimum balance between oxygen level and degree of mixing is maintained throughout the combustion zone during combustion of the sample material.

As the pressurized stream of incoming oxygen spirals downwardly through the combustion zone 11, the helical flow pattern produces centrifugal forces within the upwardly flowing gas stream which drive the combustion products against the hot walls of the cylinder 12 while constantly and thorougly mixing the gases, and any particulate matter entrained therein. The resulting turbulence and increased residence time within the combustion zone products complete reaction of the gases and particulate matter so that complete combustion is assured, as will be seen from the specific working examples to be described below. This helical and countercurrent flow pattern within the primary combustion zone achieves complete combustion with many different types of samples, both solid and liquid, and produces clean combustion products with essentially no remaining soot or unreacted gases.

Although it is not intended to limit the invention to any particular theory, it is believed that gases and entrained particulate matter flowing counter to the downwardly spiraling oxygen streams are continually centrifuged toward the outer periphery of the combustion zone. Thus, the gases and particulate material are brought into direct contact with the hot, spiraling, downflowing oxygen stream and the heated walls of the metal cylinder 12 to achieve effective mixing and heat exchange between the cylinder walls and the materials flowing therethrough. The axial flow rate near the walls of the cylinder is slower than the flow rate in the center of the tube, thereby further enhancing heat exchange between the cylinder walls and the materials flowing therethrough.

Below the crucible 10, a second oxygen feed line 33 feeds oxygen into the annular space between the cylinder 12 and the crucible platform 15 to prevent any of the radioactive combustion products from stagnating below the crucible during the combustion cycle. The ceramic crucible 10 does not form a tight seal with the cylinder 12, but any combustion products that diffuse downwardly past the crucible lip are swept back into the combustion zone 11 by the upward flow of oxygen from the feed line 33. This oxygen cannot flow downwardly because of the seal provided by the gasket 18 at the bottom of the cylinder 12. The oxygen feed rate through the line 33 is typically within the range of 0.05 to 0.2 liter/minute.

It is preferred to preheat and oxygen or oxygen-containing gas before it enters the combustion zone 11 so that it does not have any cooling effect on the combustion process. In the illustrative device, this preheating may be easily achieved by using metallic oxygen feed lines 31, 31*a* and 33 which are in contact with the heated walls of the cylinder 12. With this arrangement, the heat from the walls of the cylinder 12 is conducted through the walls of the metallic feed lines toward the oxygen source, so that the oxygen is heated by gradually incrasing temperatures as it approaches the combustion zone 11.

Figure 2:
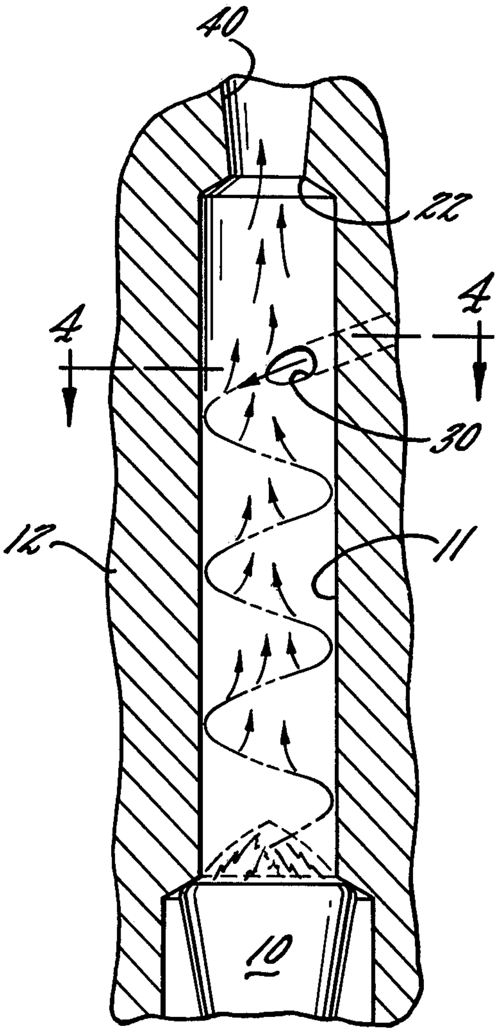
FIG. 2 is an enlarged view of the primary combustion zone in the system of FIG. 1 illustrating the gas flow patterns in the zone with a sample burning at a low flame level.
Figure 3:
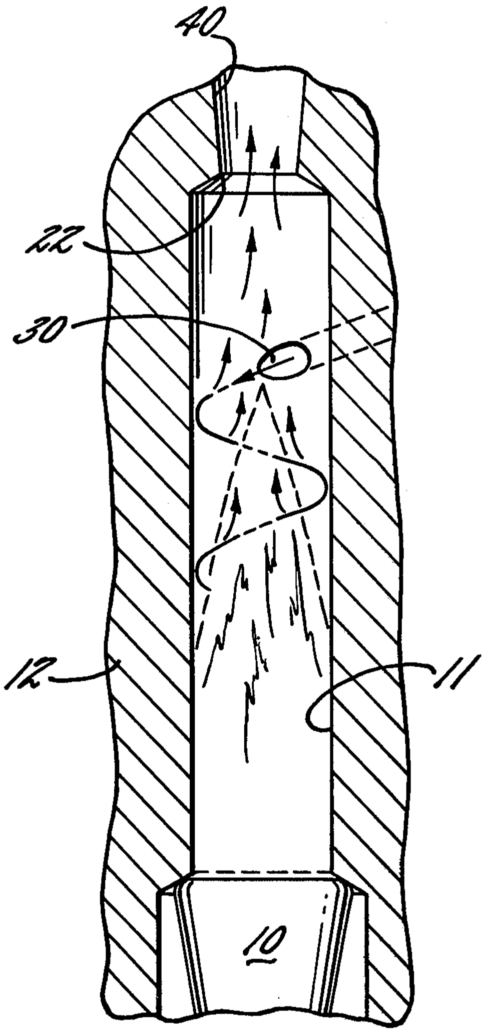
FIG. 3 is the same view shown in FIG. 2 but with the sample burning at a high flame level.

One of the significant advantages of the present invention is that the rate of combustion of the sample within the crucible 10 is automatically regulated for different types of samples, e.g., samples of different volatilities, so that the rate at which the combustion products are produced does not exceed the amount of oxygen available from a stoichiometric standpoint, even through a constant initial oxygen feed rate is used for all samples to facilitate automatic operation. This effect is attributable to the combination of the downwardly flowing oxygen stream and the radiant heating of the sample from the hot cylinder walls and from any flame produced within the combustion zone. Pyrolysis products above the crucible 10 shield the sample from the radiant heat of the hot walls of the combustion zone and any flame therein. A volatile sample or a sample with a large surface area produces pyrolysis products at a relatively high rate, producing a relatively high flame in the combustion zone (FIG. 3); consequently there is a relatively large quantity of pyrolysis products shielding the sample, causing the sample to be heated at a relatively slow rate. Also, the oxygen is completely consumed at a relatively high region of the combustion zone and no oxygen reaches the sample in the crucible, thereby further moderating the combustion of volatile samples. On the other hand, a sample with a low volatility and/or a small surface area produces pyrolysis products at a relatively low rate, producing a low flame (FIG. 2) and a relatively small quantity of pyrolysis products shielding the sample, thereby causing the sample to be heated at a relatively fast rate. The low flame also allows more oxygen to reach the sample in the crucible to further enhance combustion. Thus, the sample combustion rate is self-regulating, with the sample being shielded the most when the rate of production of pyrolysis products is the greatest, and shielded the least when the rate of production of pyrolysis products is the lowest. This phenomenon can be viewed as a negative feedback effect which varies the heat input to the sample in inverse relationship to variations in the output of pyrolysis products. This is in contrast to ordinary flame combustion where the intensity of the flame and the heating of the sample increases as the rate of generation of pyrolysis products increases so that combustion proceeds at a faster and faster rate.

Another advantage of the combustion system provided by this invention is that it is difficult for uncombusted particulate matter to escape from the primary combustion zone. Because the spiraling oxygen stream is fed into the combustion zone near the top thereof, the ascending gases and particles spin at an increasing velocity as they rise through the combustion zone toward the exhaust port 22 due to the increased velocity of the oxygen stream in the upper region of the combustion zone. Because of the restricted size of the exhaust port 22 relative to the diameter of the combustion zone 11, the gases and particles spin even faster as they converge toward the entrance to the port 22 due to the reduced radius of the spiral flow. As a consequence of this increasing spin rate in the upward flow of combustion products, any solid particles are centrifuged radially outwardly so that they cannot enter the exit port 22. Instead, the solid particles enter the downwardly spiraling oxygen stream along the walls of the combustion zone and are carried back down toward the crucible 10. The particles continue to circulate in this manner until they have been consumed or, if they are non-combustible, until they drop into the crucible at the end of the combustion cycle. The non-combustible ceramic crucible retains any residue or ash remaining at the end of the combustion cycle so that any such non-combustible material can be removed from the combustion chamber before the next sample is combusted.

The use of the insulating, non-combustible ceramic crucible in combination with the external heat source and the absence of any heat source below the crucible also avoids flash boiling of the sample, i.e., the sample is combusted gradually rather than instantaneously. This avoids the generation of gaseous products from the sample in concentrations so high that it is difficult to achieve complete combustion. That is, the concentrations of combustible materials in the gaseous state within the combustion zone are maintained at levels where complete combustion can be effected. Since the sample is heated primarily from the top, there is a temperature gradient between the top and bottom of the crucible so that the sample is combusted from the top down, thereby providing a further safeguard against flash boiling of the sample. In this connection, the relatively cool platform beneath the crucible also helps maintain the bottom of the crucible at a lower temperature than the top.

The use of a non-combustible sample container in the combustion system of this invention is made possible by the completeness of the combustion effected by the system, even at the very bottom of the sample container. This is a significant advantage because the combustible sample containers used in certain previous flame combustion systems produce additional combustion products which are of no interest but nevertheless are collected in the recovery system used to collect the radioactive nuclides of interest. Since the recovery system has a limited volume, the additional combustion products contributed by the combustible sample container have the effect of reducing the size of sample that can be combusted because of the volumetric limitations of the recovery system. Of course, the ceramic crucible 10 that is preferably used in the system of the present invention contributes no additional combustion products whatever.

A further important advantage of the combustion system provided by this invention is that relatively cool samples are introduced into the primary combustion zone and brought up to temperature gradually, while still achieving complete combustion. Consequently, the combustion is extremely safe and can be safely left unattended if automated and coupled to an automatic sample loading and unloading machanism. And yet it also achieves complete combustion of even difficult samples without any prior treatment or preparation, producing exhaust products which are essentially fre of smoke, soot or other particulate combustible matter. When combined with commercially available recovery systems of the type described in my aforementioned patents, this combustion system is capable of achieving radioactive nuclide recoveries in excess of 99% negligible memories attributable to pyrolysis products, with a wide variety of different samples.

The unitary metal vessel that forms the combustion zone also offers advantages over the glass or quartz flasks that have been used in certain prior combustion systems. The higher thermal conductivity of the metal vessel permits more rapid temperature equilibration of the combustion apparatus between samples, and is particularly advantageous in supplying heat to liquid or wet samples which tend to cool the combustion zone and extend the combustion time due to evaporation of the liquid in the sample. Th glass or quartz vessels also pose sealing and breakage problems which are not encountered with the metal vessel.

Returning now to the flow of combustion products, from the exit port 22 the combustion products pass upwardly through an outwardly flared passageway 40 which leads into an enlarged chamber 41 formed by a head member 42 fastened to the top of the body member 43 that forms the oxygen feed conduit 31*a*. The larger diameter of the chamber 41 causes a reduction in the average velocity of the ascending stream of combustion products, thereby increasing the residence time of the gases in this region to increase the probability of achieving complete combustion of even dilute concentrations and combustible materials remaining in the gas stream. The reversal in direction of flow of the combustion products from the exit port 22 to the chamber 41 also increase turbulence in the gas stream, thereby improving mixing of the combustible gases to further ensure complete combustion. The chamber 41 is heated by the same electrical heater 20 which heats the combustion zone 11 because the heater 20 extends upwardly around substantially the full length of the head member 42.

From the chamber 41, the combustion products flow downwardly through an annular passageway 44 formed by a reduced outside diameter on the upper portion of the cylinder 12, and then out through a conduit 45 in the body member 43 to an exhaust line 46 leading to the recovery system. The passageway 44 and, to a lesser extent, the conduit 45 are also maintained at relatively high temperatures so that combustion can continue in these portions of the apparatus if necessary.

While the controlled combustion system provided by this invention produces optimum concentrations of combustible gaseous materials during the major portion of the combustion cycle, it also produces relatively low concentrations at the beginning and the end of each combusting cycle. When the concentration is below a certain threshold level at a given oxygen level and a given temperature, combustion cannot be initiated or sustained; consequently, gaseous products emanating from the sample at these concentration levels pass through the system without ever being combusted. However, with the combustion system produced by this invention, it has been found that this threshold concentration level is extremely low, so that the losses due to lack of combustion of the sample are practically negligible. More specifically, the spiraling countercurrent flow of oxygen and combustion products provides a sufficient degree of turbulence and a sufficiently long residence time that even dilute concentrations of combustible gases are combusted. Also, the diminished or nearly stagnant oxygen flow rate near the crucible 10 provides a favorable fuel/oxygen ratio and longer residence time when only a small amount of lean pyrolytic products are leaving the crucible. And the restricted exit port 22 followed by the enlarged chamber 41 further contribute to the low threshold concentration at which complete combustion can be realized.

A thermostat 47 mounted in a cavity in the wall of the cylinder 12 is generally set to maintain a temperature of about 900° C. at that point. This thermostat 47 controls the electrial heater 20 to supply sufficient heat to maintain the temperature sensed by the thermostat at the selected temperature.

The following working examples will illustrate the results achieved by the use of this invention with a variety of different sample materials. In each of these examples, the combustion apparatus has a combustion zone 50 millimeters long with a diameter of 13 millimeters and a wall thickness of 12 millimeters directly above the crucible 10. The exit port 22 at the top of the combustion zone had a diameter of 6 millimeters, the bore 40 above the exit port 22 was 30 millimeters long with a maximum diameter of 14 millimeters, and the chamber 41 was 30 millimeters long with an inside diameter of 30 millimeters and a wall thickness of 3 millimeters. The cylinder 12, the body member 43 and the head member 42 were all formed of Kanthal, which is stable at temperatures up to at least about 1400° C. In the lower portion of the cylinder forming the combustion zone, the chamber containing the sample crucible was 65 millimeters long with a diameter of 20 millimeters and the tapered bore at the very bottom of the cylinder was 15 millimeters long.

EXAMPLE 1

Using a system of a type illustrated in the drawings and having the dimensions described above, 1000 milligrams of plain wet soil containing $14_C$-labelled glucose (without any prior treatment or preparation) was loaded into the combustion zone at room temperature. Pressurized pure oxygen was fed from a pressurized source (60 psi) through a needle valve into the primary combustion zone at a feed rate of 3 liters per minute, and the thermostat for the combustion vessel was set at 950° C. The actual temperature of the primary combustion zone was approximately 900° C., and the temperature of the secondary combustion zone was approximately 200° C. higher. The $14_C$ in the combustion products was recovered using the recovery system of a commercial Model 306 sample oxidizer made by Packard Instrument Company, Inc., modified to include a restriction between the carbon reaction column and the carbon exchange column to produce at 3 psi pressure drop to improve the recovery of $14_C$ from the slow-burning sample by expanding and cooling the vapors exiting from the reaction column. The resulting recovery of $14_C$ was 99% with a memory of less than 0.02% and a spillover of 0.02%.

EXAMPLE 2

Using a system of a type illustrated in the drawings and having the dimensions described above, 300 milligrams of plain $14_C$-labelled plamitic acid (without any prior treatment or preparation) was loaded into the combustion zone at room temperature. Pure oxygen was fed into the primary combustion zone at an initial feed rate of 4 liters per minute, and the thermostat for the combustion vessel was set at 850° F. As before, the maximum temperature of the secondary combustion zone was about 200° C. above that of the primary zone. Using the recovery system of a commercial Model 306 sample oxidizer made by Packard Instrument Company, Inc., the recovery of $14_C$ was 99.34% with a memory of less than 0.02% and a spillover of 0.02%.

We claim as our invention:

1. A process for combusting materials containing radioactive nuclides to permit recovery of the radioactive nuclides, said process comprising the steps of combusting a sample material containing at least one radioactive nuclide in a combustion zone while continuously exhausting combustion products from one end of the combustion zone, introducing a continuous pressurized stream of oxygen-containing gas into the combustion zone between the exhaust end of said zone and the sample during the combustion thereof, and directing at least a portion of the pressurized oxygen-containing gas stream through the combustion zone in a spiral path toward said sample to circulate at least a portion of the combustion products around the combustion zone as they flow towad the exhaust end of said zone counter to the flow of the spiraling stream of oxygen-containing gas, whereby said combustion products are intimately mixed with said oxygen-containing gas in said combustion zone.

2. A combustion process as set forth in claim 1 wherein said sample material is contained in a non-combustible crucible in said combustion zone so that the crucible does not contribute to the combustion products.

3. A combustion process as set forth in claim 1 wherein the combustion zone is formed by metal walls, and the sample is combusted by heating said metal walls.

4. A combustion process as set forth in claim 3 wherein said metal walls are heated by conduction from a heat source disposed around said walls.

5. A combustion process as set forth in claim 1 wherein the combustion products are exhausted from the primary combustion zone through a restricted exit port having a cross sectional opening considerably smaller than that of the primary combustion zone.

6. A combustion process as set forth in claim 5 wherein the combustion products are discharged from said exit port into a chamber having a cross section considerably larger than that of said exit port.

7. A combustion process as set forth in claim 3 wherein the pressurized stream of oxygen-containing gas is introduced into the combustion zone through a metallic conduit in contact with the metal forming the walls of said combustion zone so that at least a portion of said conduit is heated by heat from the combustion zone to preheat the oxygen-containing gas.

8. A combustion process as set forth in claim 1 wherein the sample material contains at least one radioactive nuclide selected from the group consisting of tritrium and carbon-14.

9. A combustion process as set forth in claim 1 wherein said oxygen-containing gas is substantially pure oxygen.

10. A combustion process as set forth in claim 1 wherein the combustion zone is heated to a temperature in the range of from about 700° C. to about 1000° C.

11. A combustion process as set forth in claim 1 wherein said combustion zone has a generally circular cross section, and said pressurized stream of oxygen-containing gas is introduced tangentially with respect to the walls of said combustion zone.

12. Apparatus for combusting materials containing radioactive nuclides to permit recovery of the radioactive nuclides, said apparatus comprising the combination of a combustion zone for combusting a sample material containing at least one radioactive nuclide, means for continuously exhausting combustion products from one end of the combustion zone, means for introducing a continuous pressurized stream of oxygen-containing gas into the combustion zone between the exhaust end of said zone and the sample during the combustion thereof and directing at least a portion of the pressurized gas stream through the combustion zone in a spiral path toward said sample to circulate at least a portion of the combustion products around the combustion zone as they flow toward the exhaust end of said zone counter to the flow of the spiraling stream of oxygen-containing gas, whereby said combustion products are intimately mixed with said oxygen-containing gas in said combustion zone.

13. Combustion apparatus as set forth in claim 12 wherein the combustion zone has metal walls, and including means outside the combustion zone for heating said metal walls to a temperature sufficiently high to combust the sample.

14. Combustion apparatus as set forth in claim 13 wherein said heaing means comprises a heat source disposed around said metal walls for heating the walls by conduction.

15. Combustion apparatus as set forth in claim 12 which includes a restricted exit port at the top of the combustion zone, said exit port having a cross sectional opening considerably smaller than that of the primary combustion zone.

16. Combustion apparatus as set forth in claim 15 which includes a chamber receiving the combustion products discharged from said exit port, said chamber having a cross section considerably larger than that of said exit port.

17. Combustion apparatus as set forth in claim 13 wherein the means for introducing the pressurized stream of oxygen-containing gas into the combustion zone comprises a metallic conduit in contact with the metal forming the walls of said combustion zone so that at least a portion of said conduit is heated by heat from the combustion zone to preheat the oxygen-containing gas.

18. Combustion apparatus as set forth in claim 12 wherein the primary combustion zone has a generally circular cross section, and said pressurized stream of oxygen-containing gas is introduced tangentially with respect to the walls of said combustion zone.

* * * * *